(12) United States Patent
Kantomaa

(10) Patent No.: US 8,333,586 B2
(45) Date of Patent: Dec. 18, 2012

(54) ORTHODONTIC BRACKET AND ARRANGEMENT FOR CORRECTING IRREGULARITIES OF THE TEETH

(76) Inventor: Tuomo Kantomaa, Kello (FI)

( * ) Notice: Subject to any disclaimer, the term of this patent is extended or adjusted under 35 U.S.C. 154(b) by 0 days.

(21) Appl. No.: 13/254,140

(22) PCT Filed: Mar. 5, 2010

(86) PCT No.: PCT/FI2010/050170
§ 371 (c)(1),
(2), (4) Date: Aug. 31, 2011

(87) PCT Pub. No.: WO2010/103178
PCT Pub. Date: Sep. 16, 2010

(65) Prior Publication Data
US 2011/0311934 A1    Dec. 22, 2011

(30) Foreign Application Priority Data
Mar. 10, 2009    (FI) .................... 20095239

(51) Int. Cl.
*A61C 7/28* (2006.01)
(52) U.S. Cl. ........................................ 433/10
(58) Field of Classification Search ................ 433/8, 9, 433/10, 11, 13, 14
See application file for complete search history.

(56) References Cited

U.S. PATENT DOCUMENTS

| 4,077,126 A | 3/1978 | Pletcher |
| 4,419,078 A | 12/1983 | Pletcher |
| 4,655,708 A | 4/1987 | Fujita |
| 5,738,513 A * | 4/1998 | Hermann ........................ 433/13 |
| 6,942,483 B2 | 9/2005 | Heiser |
| 7,204,690 B2 * | 4/2007 | Hanson .......................... 433/10 |
| 7,214,057 B2 | 5/2007 | Voudouris |
| 7,396,230 B2 | 7/2008 | Abels et al. |
| 2004/0209219 A1 | 10/2004 | Miyaji et al. |
| 2009/0130621 A1 * | 5/2009 | Chikami ........................ 433/10 |

FOREIGN PATENT DOCUMENTS

EP    0 440 478 A2    8/1991

OTHER PUBLICATIONS

International Search Report for parent application PCT/FI2010/050170, having a mailing date of Jun. 11, 2010.
Finnish Search Report for priority application FI 20095239, dated Oct. 15, 2009.

* cited by examiner

*Primary Examiner* — Ralph Lewis
(74) *Attorney, Agent, or Firm* — Andrus, Sceales, Starke & Sawall, LLP

(57) ABSTRACT

An orthodontic bracket having a body portion with an archwire slot for receiving an archwire. The bracket includes a locking portion slot wherein the archwire slot is situated in the wall of the locking portion slot. A locking portion can be rotated into at least two of the following positions: standby position, in which the setting slot of the locking portion is towards the opening on the surface facing away from the tooth, and transfer position, in which the setting slot is towards the archwire slot or locking position, in which the locking portion closes the archwire slot at least partially. The archwire can be placed in the setting slot when the locking portion is in standby position, and the archwire can be placed in the archwire slot when the locking portion is in transfer position, and in the locking position the locking portion is arranged to hold the archwire in place in the archwire slot.

23 Claims, 12 Drawing Sheets

ORTHODONTIC BRACKET AND ARRANGEMENT FOR CORRECTING IRREGULARITIES OF THE TEETH

CROSS-REFERENCE TO RELATED APPLICATIONS

This application is the U.S. national stage application of International Application No. PCT/FI2010/050170, filed Mar. 5, 2010, which International application was published on Sep. 16, 2010 as International Publication No. WO 2010/103178 A1 in the English language and which application is incorporated herein by reference. The International application claims priority of Finnish Patent Application No. 20095239, filed Mar. 10, 2009, which application is incorporated herein by reference.

BACKGROUND

The invention relates to an orthodontic bracket, which comprises a body portion and a locking portion, and in the body portion there is an archwire slot for an archwire, and in the orthodontic bracket there is a surface against the tooth and a surface facing away from the tooth. The invention relates also to an arrangement for correcting irregularities of the teeth, which arrangement comprises orthodontic brackets to be attached to the teeth and an archwire to focus force to the orthodontic brackets.

In orthodontics fixed devices and detachable devices are used. Fixed devices are comprised of orthodontic brackets and tubes that are attached to the surface of the tooth generally with glue so that the base of the body of the orthodontic bracket or tube is against the tooth, and archwire, which is attached to the brackets and the ends of the archwire are placed in the tubes. The archwire focuses force to the orthodontic brackets and at the same time to the teeth, with which force the teeth are tried to move to their desired places. The tubes are generally last in the bracket rows at both ends. The orthodontic brackets are generally made of metal. The archwire is generally made of metal and the archwire has some shape to which it attempts to return if it is placed under strain.

There is a slot in the body of the orthodontic bracket, in which the archwire is placed. Generally this slot is angular, the three walls of which are in cross section of the slot substantially perpendicular towards each other. Furthermore in the bracket there are parts with the help of which the archwire is fastened to the slot and parts to which tighteners can be attached to add traction between the brackets, such as for example rubber bands or metal ligature wires. Traditionally the archwire is tied to the slot with binding material by using the tie wings at the upper and lower part of the bracket as the support members of the binding material. Metal or rubber ligature wires or rubber ligatures can be used as binding material. Also brackets in which the archwire is locked in place over by a slidable or rotatable locking arrangement moved over the archwire slot. Also in these brackets tie wings are needed for placing the tighteners.

In FIG. 1 an example is presented of an orthodontic bracket according to prior art. In the orthodontic bracket there is a surface 101 against the tooth and a surface 102 facing away from the tooth. There is a slot 103 in the orthodontic bracket for the archwire. The slot is perpendicular. There are two tie wings 104 which are curved towards the surface of the tooth on both sides of the slot for the archwire to be attached to the slot.

In FIG. 2 there is the orthodontic bracket of FIG. 1 attached to the surface 201 of the tooth and as seen above. The orthodontic bracket is attached generally with glue or a corresponding substance to the tooth. The archwire 202 is placed in the slot 103. The fixing wire 203 holds the archwire in place. The fixing wire runs under the tie wings 104 and over the archwire. The orthodontic brackets are attached usually to several teeth and the archwire is attached to each bracket. When the archwire is attached it is under strain and it focuses force to the orthodontic brackets and through them to the teeth.

Tighteners, which are usually loops made out of elastic material, that cause additional traction can be attached between the orthodontic brackets. These tighteners are attached in the case according to the example to the tie wings 104. Since also the fixing wire 203 of the archwire has to be placed on the tie wings, the orthodontic bracket's profile becomes inevitably high. Also space must be reserved for the placing of fixing wire and possible tighteners, in other words the ends of the tie wings cannot be very close to the surface of the teeth.

In FIG. 3 there is an example of an arrangement for correcting irregularities of the teeth. The arrangement is comprised of orthodontic brackets 301, archwire 302, tighteners 303 and tubes 304. The orthodontic brackets are attached to the teeth 305. Orthodontic brackets are placed in the case according to the example on the buccal side of the teeth, but they can also be placed on the lingual side of the teeth. The archwire is generally attached to all orthodontic brackets. The archwire is under strain and it focuses force to the teeth, which force gradually shifts the teeth towards the desired position or orientation. The ends of the archwire are placed in the so called tubes at the end of the row. Additional traction can be created between the orthodontic brackets with tighteners. The tighteners are attached on the projections of the orthodontic brackets.

At the beginning of the orthodontic treatment usually small archwires with circular cross sections are used to shift the teeth into a row. In most cases the wire is switched at some point of the treatment. At that time an angular archwire can be placed in the slot. If the walls of the angular archwire and the walls of the slot are diverging, the archwire causes with the help of the orthodontic bracket a torque force to the tooth which shifts the root of the tooth. When the upper and lower surfaces of the angular archwire are parallel to the occlusion level, the archwire torques the lower and upper surface of the bracket slot parallel to the occlusion level. When the surfaces of the bracket slot and the tooth are in the predetermined angle in relation to each other, the surface of the tooth can be set to a desired orientation in relation to the occlusion level.

The brackets can be attached to all of the teeth. Generally a different type of bracket is needed for each tooth because the torque angle of the archwire slot of each bracket is different for each tooth depending on which position the tooth is desired to be after the treatment is over. Also the width and thickness as well as the shape of the base of the bracket varies according to the teeth. The brackets can also be attached on the front and rear surfaces of the teeth, whereupon the forming and other variables of the base of the orthodontic bracket are also different.

A particular challenge for the brackets used on the rear surfaces of the teeth is that the brackets must have be as low profiled as possible to fit between the upper and lower teeth in the region of the incisors and obstruct as little as possible the tongue. Furthermore the placement of the archwire and the tighteners should be simple, because working on the lingual surfaces of the teeth is difficult.

An orthodontic bracket is known form patent publication U.S. Pat. No. 6,942,483 in which the archwire is held in place by a closing spring structure. The assembly becomes quite high profiled. In this solution there needs to also be tie wings in the orthodontic bracket for tighteners.

From patent publication U.S. Pat. No. 7,214,057 an orthodontic bracket is known, in which the archwire is held in its place by a curved plate arrangement. There is an opening at the lower part of the orthodontic bracket in which the elongated portion of the plate arrangement is placed and the curved portion of the plate arrangement sits over the orthodontic bracket, in which this curved portion keeps the archwire in the slot. Using the curved plate arrangement and the tie wings makes the orthodontic bracket high profiled, whereby it readily disturbs the user and the archwire is left quite far from the surface of the tooth.

An orthodontic bracket is known from patent publication U.S. Pat. No. 7,396,230 in which the archwire is held in place by a flexible cover fixed to the orthodontic bracket. The cover is fixed from its one end to the surface of the orthodontic bracket and it can be flexibly deformed over the surface of the orthodontic bracket that faces away from the tooth and the protrusion on the cover attaches on the groove in the orthodontic bracket and the cover thus keeps the archwire in place in either said groove or in a slot meant for the archwire. Further there is a hook in the orthodontic bracket for additional fasteners. Orthodontic bracket structure according to the publication makes it high profiled, which impedes the mounting and use for example on the lingual surfaces of the teeth.

SUMMARY

An objective of the invention is a solution, with which the disadvantages and defects associated with the prior art can be significantly reduced.

The goals according to the invention are achieved with an orthodontic bracket and an arrangement for correcting irregularities of the teeth, which are characterised by what is set forth in the independent claims. Some preferred embodiments of the invention are presented in the dependent claims.

The orthodontic bracket according to the invention comprises a body portion and a locking portion. In the orthodontic bracket in the body portion there is a surface against the tooth and a surface facing away from the tooth. In the body portion there is at least one archwire slot for the archwire. There is a locking portion slot in the body portion, which slot is open towards the surface of the orthodontic bracket facing away from the tooth, whereupon it forms an opening on the said surface, and at least one archwire slot is situated in the wall of the locking portion slot. There is at least one setting slot in the locking portion, which slot is arranged when rotating the locking portion to align at least towards the archwire slot or the extension defined by it or towards the opening on the surface facing away from the tooth or the extension defined by it. By alignment of the setting slot towards something is here meant that it opens towards something.

The locking portion is fixed to the body portion so that the rotation axis of the locking portion is aligned so that when the archwire is in the setting slot the locking portion can be rotated.

In the orthodontic bracket according to the invention the locking portion slot is substantially parallel to the archwire slot. Locking portion slot is arranged to penetrate the body portion at least partially. The archwire slot of the orthodontic bracket can act as a tube covering the end of the archwire when necessary. The setting slot of the locking portion is dimensioned so that one or several tighteners or archwires or both can be placed in the setting slot.

In an embodiment of the invention there is a lever arrangement in the locking portion for rotating the locking portion. In another embodiment of the invention a means can be attached on the locking portion for rotating the locking portion. In this case there is for example an opening or a hole in the locking portion, into which the rotating means can be placed. When the locking portion has been rotated the rotating means can be removed.

In a third embodiment of the invention there are holes or corresponding formings in the surface of the body portion against the tooth to enhance attachment of the orthodontic bracket to the tooth. Holes can also be added to the sides of the orthodontic bracket, whereupon the adhesive material, such as glue or cement, can be applied also to the sides of the bracket. When hardened the adhesive material keeps the orthodontic bracket in place and supports it also from the sides. The applying of the adhesive material to the sides of the orthodontic bracket is done so that rotating the locking portion is not hindered.

In the orthodontic bracket according to the invention there is a locking mechanism with which the locking portion can be locked into such a position that the locking portion closes the archwire slot at least partially. In an embodiment according to the invention this locking mechanism is implemented with formings of the body portion and the locking portion.

The orthodontic bracket can be attached to both the front and rear surfaces of the tooth.

Arrangement for correcting irregularities of the teeth according to the invention comprises orthodontic brackets to be attached to teeth, which brackets comprise a body portion and a locking portion, and in the body portion there is an archwire slot for an archwire, and in the body portion there is a surface against the tooth and a surface facing away from the tooth. Further the arrangement comprises an archwire to focus force to the orthodontic brackets. In the body portion of the orthodontic brackets comprised in the arrangement there is a locking portion slot. This locking portion slot forms an opening on the surface facing away from the tooth. In the body portion there is at least one archwire slot, of which at least one is situated in the wall of the locking portion slot. The locking portion can be attached to the body portion so that is can be rotated. There is at least one setting slot in the locking portion. The locking portion is arranged to be rotatable to at least two of the following positions: standby position, in which the setting slot is towards the opening on the surface facing away from the tooth, transfer position, in which the setting slot is towards the archwire slot or to a locking position, in which the locking portion closes the archwire slot at least partially. The locking portion can be either wholly or partially in the locking portion slot, but it is possible to position so that the locking portion is outside the locking portion slot. The locking portion is fixed to the body portion so that the rotation axis of the locking portion is aligned so that when the archwire is in the setting slot the locking portion can be rotated.

The orthodontic bracket is arranged so that the unattached archwire can be placed in the setting slot of the locking portion, when the locking portion is in standby position, and the archwire can be placed in the archwire slot when the locking portion is in transfer position. In locking position the locking portion is arranged to hold the archwire in place in the archwire slot.

In an embodiment of the arrangement according to the invention the locking portion is arranged to close at least partially the opening on the surface facing away from the tooth in locking position.

In another embodiment of the arrangement according to the invention the locking portion is arranged to close the archwire slot at least partially in the standby position.

In a third embodiment of the arrangement according to the invention the orthodontic bracket is arranged so that in the locking portion standby position one or several tightenings or a second archwire or one or several of both can be placed in the locking portion setting slot. The locking portion can then be moved to the locking position, whereupon the tighteners or the archwire placed in the setting slot are fixed to the setting slot.

In an embodiment of the arrangement according to the invention the archwire can be placed in place when the locking portion is in locking position. Then the end of the archwire is placed in the archwire slot or setting slot from the side of the orthodontic bracket. In this case the bracket functions as a tube.

In an embodiment of the arrangement according to the invention the orthodontic bracket is arranged so that the locking portion can be rotated from standby position to locking position without it being in the transfer position there in between.

In the arrangement according to the invention the archwire or archwires that have been set in place are arranged to focus force to the orthodontic brackets. The amount and orientation of the force depend on the stress of the archwire and the position of the archwire slot.

In the arrangement according to the invention the size and shape of the orthodontic brackets can be adapted for each tooth when necessary. The archwire slot can be placed in the body portion in different positions for each orthodontic bracket to focus different kinds of forces on the tooth. The arrangement according to the invention can be mounted on the buccal or lingual surfaces of the teeth.

An advantage of the invention is that is facilitates an easy and quick placement of the archwire on the orthodontic brackets. Also removing and changing the archwire becomes easier.

Further an advantage of the invention is that the orthodontic brackets can be made lower and without sharp forms compared to previous solution, in which case they interfere less the cheeks and lips when placed on the front surface of the teeth and the tongue when placed on the rear surface of the teeth. The invention can be implemented also without hooks and tie wings.

An advantage of the invention is also that the locking mechanism of the archwire is protected inside the body.

Further the invention facilitates that with it the archwire can be placed nearer to the surface of the tooth than in previous solutions.

An advantage of the invention is also that it facilitates the use of additional tighteners without separate tie wings on the brackets. Furthermore the additional tighteners stay in place more securely than when attached to tie wings. The invention facilitates also the simultaneous use of two archwires.

BRIEF DESCRIPTION OF THE DRAWINGS

The prior art was described with reference to FIGS. 1, 2 and 3. The invention is described in detail with reference to FIGS. 4-24, in which.

DETAILED DESCRIPTION OF THE DRAWINGS

Figure 1:
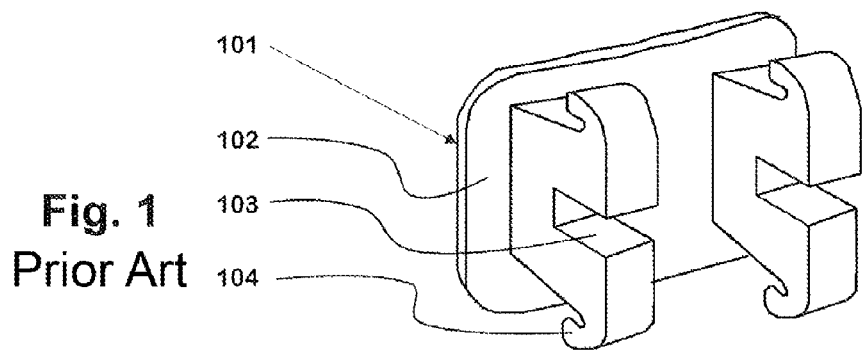
FIG. 1 presents as an example an orthodontic bracket according to prior art.
Figure 2:
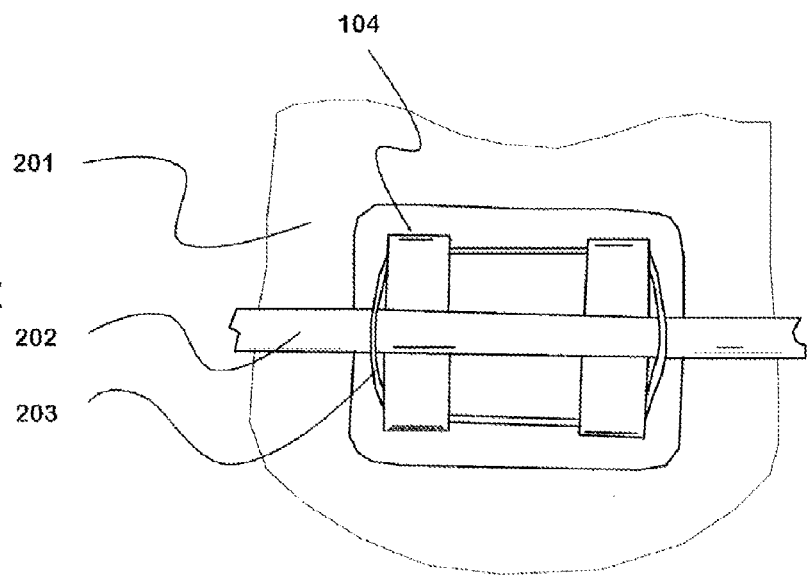
FIG. 2 presents as an example an orthodontic bracket presented in FIG. 1, seen from above, according to prior art.
Figure 3:
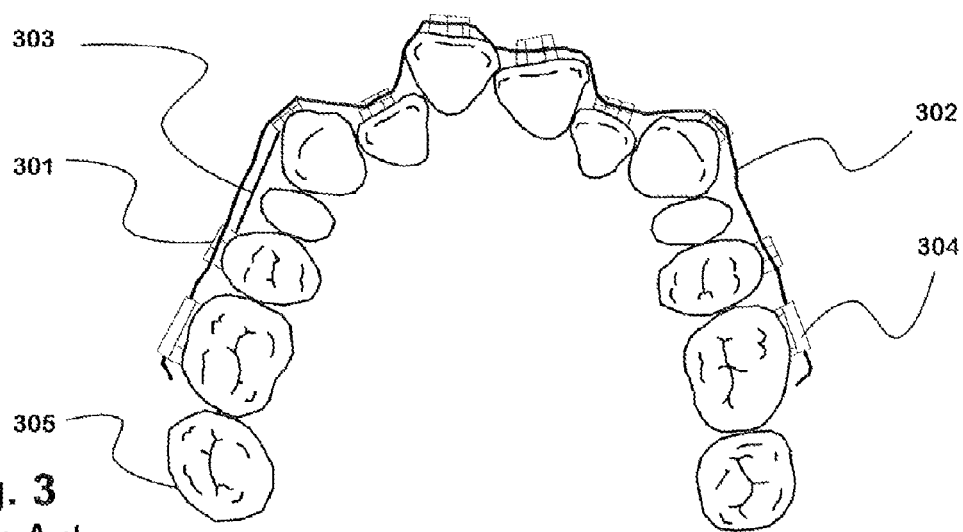
FIG. 3 presents as an example the use of orthodontic brackets.
Figure 4:
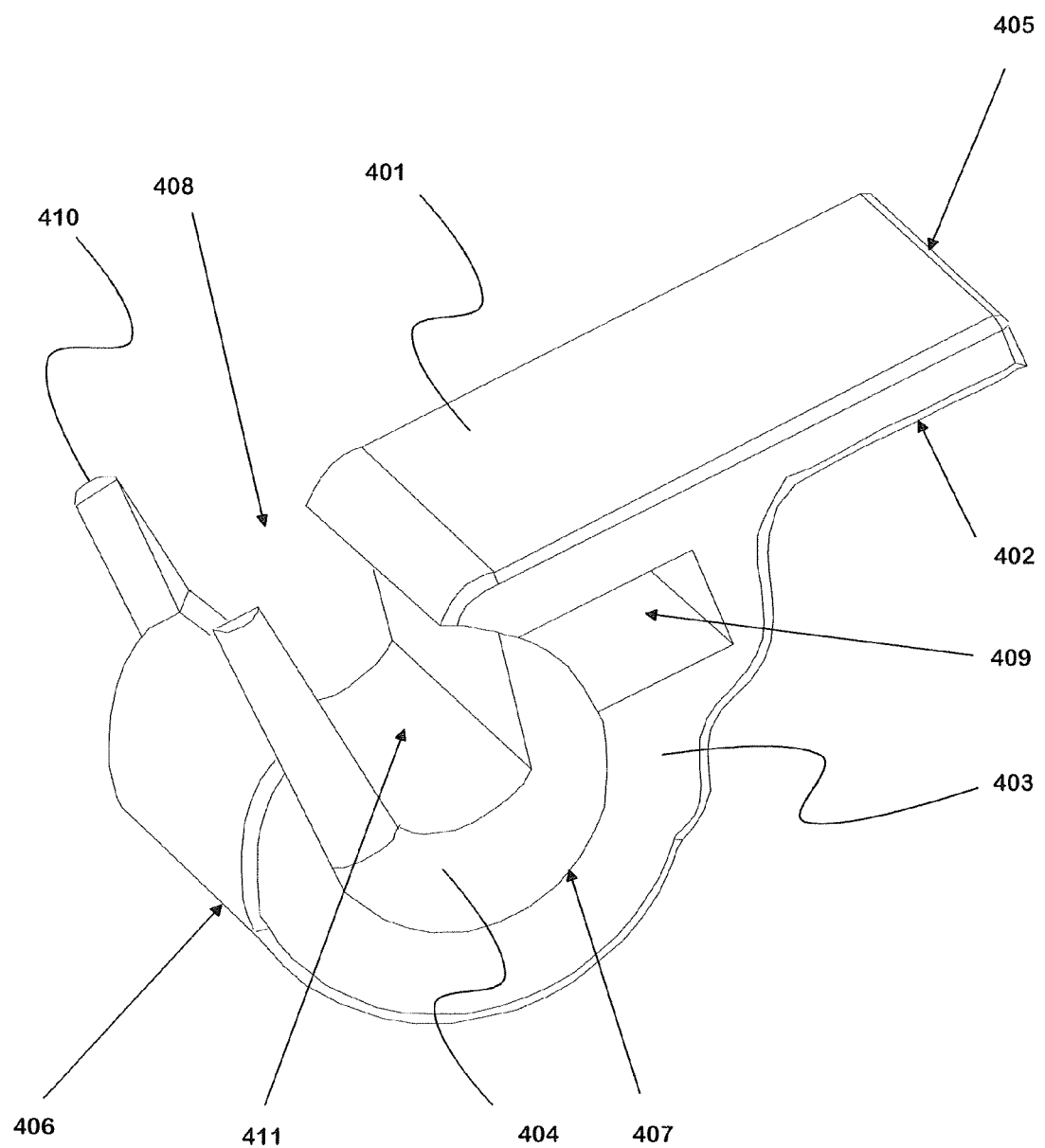
FIG. 4 presents as an example an orthodontic bracket according to the invention.

FIG. 4 presents as an example an orthodontic bracket according to the invention. In the orthodontic bracket there is a surface 401 facing away from the tooth and a surface 402 against the tooth. The orthodontic bracket has side surfaces. The orthodontic bracket is attached to the tooth from the surface placed against the tooth. In the attachment as the adhesive material usually glue or some substance that hardens is used. The surface facing away from the tooth is smooth. The surface against the tooth has substantially the shape of the tooth to which the orthodontic bracket is meant to be attached. Furthermore the shaping of the surface against the tooth depends on whether the orthodontic bracket is meant for the front or the rear surface of the tooth. Holes can have been made to the surface placed against the tooth so that the there would be more contact surface for the adhesive substance. These holes can be made also on the sides of the orthodontic bracket, if the adhesive material is spread also around the orthodontic bracket. In the orthodontic bracket there are an end 405 facing towards the point of the tooth (occlusal end) and an end 406 facing towards the gingiva (gingival end). These directions refer to the orientation into which the orthodontic bracket is meant to be placed.

In the orthodontic bracket there is a body portion 403 and a movable locking portion 404. In the body portion there is a locking portion slot 407. This locking portion slot opens to the surface away from the tooth 401 forming an opening 408 to it. In the orthodontic bracket the locking portion is placed in the locking portion slot. In the case according to the example the locking portion slot has substantially the same shape as the locking portion. In this case the locking portion slot and at least a part of the locking portion are curved, whereby the locking portion is easy to move, and no gaps are left between the locking portion and the walls of the locking portion slot. The locking portion slot is substantially parallel to the archwire slot. This direction is substantially transverse in relation to the body portion's axis running parallel to the tooth. Locking portion slot penetrates the body portion at least partially. In the locking portion slot, at the edges of the body portion there can be protrusions or other contours. These are for guiding and holding in place the locking portion in the locking portion slot. In the case according to the example the locking portion slot is near the gingival end 406 of the body portion and substantially has the shape of circular arch. The locking portion slot can also have a different shape. Advantageously the locking portion slot is located at the gingivalend of the orthodontic bracket, because then the locking portion is better protected, and because in some forms of the orthodontic bracket the locking portion slot and the locking portion placed in it make that part higher than the rest of the orthodontic bracket, and nearer to the gingiva it interferes less. The locking portion can also be placed in the middle of the orthodontic bracket or on the occlusal end. The locking portion slots can have in different cases different shapes.

In the locking portion slot 407 there is an archwire slot 409. In the case according to the example the archwire slot is in the locking portion slot on the side of the occlusal end 405 of the orthodontic bracket. The archwire slot can be placed in different parts of the locking portion slot. The archwire slot runs in the case according to the example through the body portion substantially parallel to the surfaces of the body portion. The archwire slot can also have other orientations. It can be for example oblique in relation to the surface of the tooth. The archwire slot is substantially perpendicular. In some applications the archwire slot can have some other shape. The orientation of the archwire slot, that is in which angle the walls of the archwire slot are in relation to the surfaces of the orthodontic bracket, can vary according to which tooth the orthodontic bracket is meant to be mounted and what kind of force is meant for the archwire in the archwire slot to focus on the tooth in which the orthodontic bracket is attached to. There may be several archwire slots in the orthodontic bracket.

The locking portion 404 of the orthodontic bracket is substantially shaped so that it fits at least partially to the locking portion slot 407 and can be moved in it. In the case according to the example the cross section of the locking portion has the shape of a circular arch. Then the part of the locking portion in the locking portion slot also has a cross section shaped like the circular arch. The locking portion has in the case according to the example substantially the same width as the body portion 403. The locking portion can also be wider or narrower than the body portion. There is a lever arrangement 410 in the locking portion for rotating the locking portion in the locking portion slot. In the case according the example there is an elongated projection on both ends of the locking portion, focusing force on which projection the locking portion can be rotated. The projections extend over the surfaces and sides of the orthodontic bracket so that it extends over the surface of the orthodontic bracket facing away from the tooth for engaging with them. In an arrangement the lever arrangement may extend also to the other direction, whereby the one end of the lever arrangement may be arranged to hold the archwire tighter in place.

There are other solutions for moving the locking portion. In the locking portion there may for example be an opening into which some means is placed with which the locking portion can be turned. The body portion and the locking portion are shaped so that the locking portion can be locked in place, whereupon it cannot move by accident. That end of the body portion in which the locking portion slot is situated is substantially rounded on its outer surface.

There is a setting slot 411 in the locking portion 404. The setting slot runs through the whole locking portion substantially parallel to the locking portion. When the locking portion is rotated the setting slot moves. The locking portion may be rotated into such positions that the setting slot opens to the opening 408 on the surface facing away from the tooth or that the setting slot opens to the archwire slot 409 or that the setting slot is against the wall of the locking portion slot. These positions of the locking portion are in this example a standby position, transfer position and a locking position. In the case according to FIG. 4 the locking portion is in standby position. There may be several setting slots in the locking portion.

Figure 5:
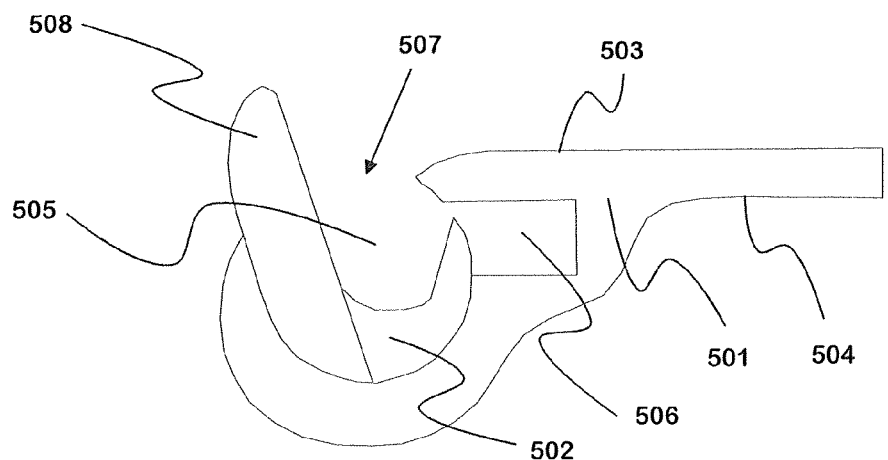
FIG. 5 presents a cross section of an orthodontic bracket according to the invention, the locking portion of which bracket is in standby position.

In FIG. 5 a cross section of an orthodontic bracket is presented as an example, which bracket is in standby position. The orthodontic bracket has a body portion 501, a locking portion 502, a surface 503 facing away from the tooth, a surface 504 against the tooth, setting slot 505 and an archwire slot 506. There is an opening 507 on the surface facing away from the tooth. There is a lever system 508 in the locking portion. The locking portion has been rotated with the lever system into such a position that the setting slot is aligned with the opening on the surface facing away from the tooth. Then an archwire or tightener or the like can be inserted into the orthodontic bracket. If the tightener is for example a rubber band or similarly shaped object, it is placed in the setting slot so that a part of the band is in the setting slot and a part is on the outer surface of the body portion. In the case according to the example the rubber band can be arranged to go around the lever system. The other end of the rubber band can be attached in a similar fashion to some other orthodontic bracket that is in the standby position. In the standby position the locking portion covers at least partially the archwire slot, whereby in the case according to the invention the wall of the locking portion forms a fourth wall to the perpendicular archwire slot and thereby the archwire slot is a tubular structure.

Figure 6:
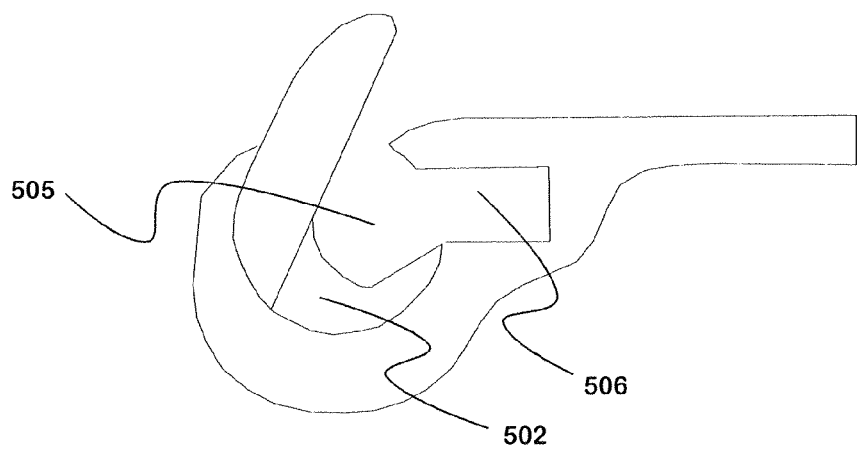
FIG. 6 presents a cross section of the orthodontic bracket according to FIG. 5, the locking portion of which is in transfer position.

In FIG. 6 a cross section of an orthodontic bracket according to FIG. 5 is presented as an example, which bracket is in transfer position. The locking portion 502 has been rotated so that the setting slot 505 has moved to alignment with the archwire slot 506. If an archwire has been inserted into the setting slot in the standby position, it can now be placed in the archwire slot. After the archwire has been set the locking portion can be rotated to the standby position according to FIG. 5, whereby the wall of the locking portion closes the archwire slot. Then the archwire in the archwire slot stays in place. In the transfer position also a previously in the archwire slot seated archwire can be removed.

Figure 7:
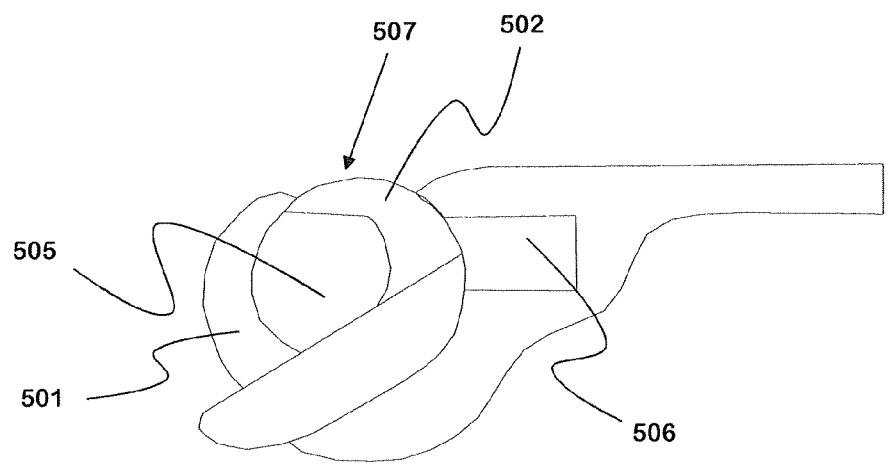
FIG. 7 presents a cross section of the orthodontic bracket according to FIG. 5, the locking portion of which is in locking position.

In FIG. 7 a cross section of an orthodontic bracket according to FIG. 5 is presented as an example, which bracket is in locking position. The locking portion 502 has been rotated from the standby position so that the locking portion closes the archwire slot 506 and the opening 507 on the surface facing away from the tooth and the setting slot 505 is against the wall of the locking portion slot of the body portion 501. Advantageously in the locking position the setting slot opens against the opposite wall of the locking portion slot than the archwire slot. Then the setting slot has been transformed into a closed tubular structure. If an archwire or a tightener has been placed in the setting slot in the standby position, it stays in place in the locking position. There is a locking system in the orthodontic bracket so that the locking portion stays in place in the locking position and does not move by accident. This can be implemented for example by formings of the body portion 501 and the locking portion 502 so that for freeing the locking portion from locking position some procedure has to be performed or enough of force has to be focused on it in the right direction. These formings can be for example suitable grooves and projections.

Figure 8:
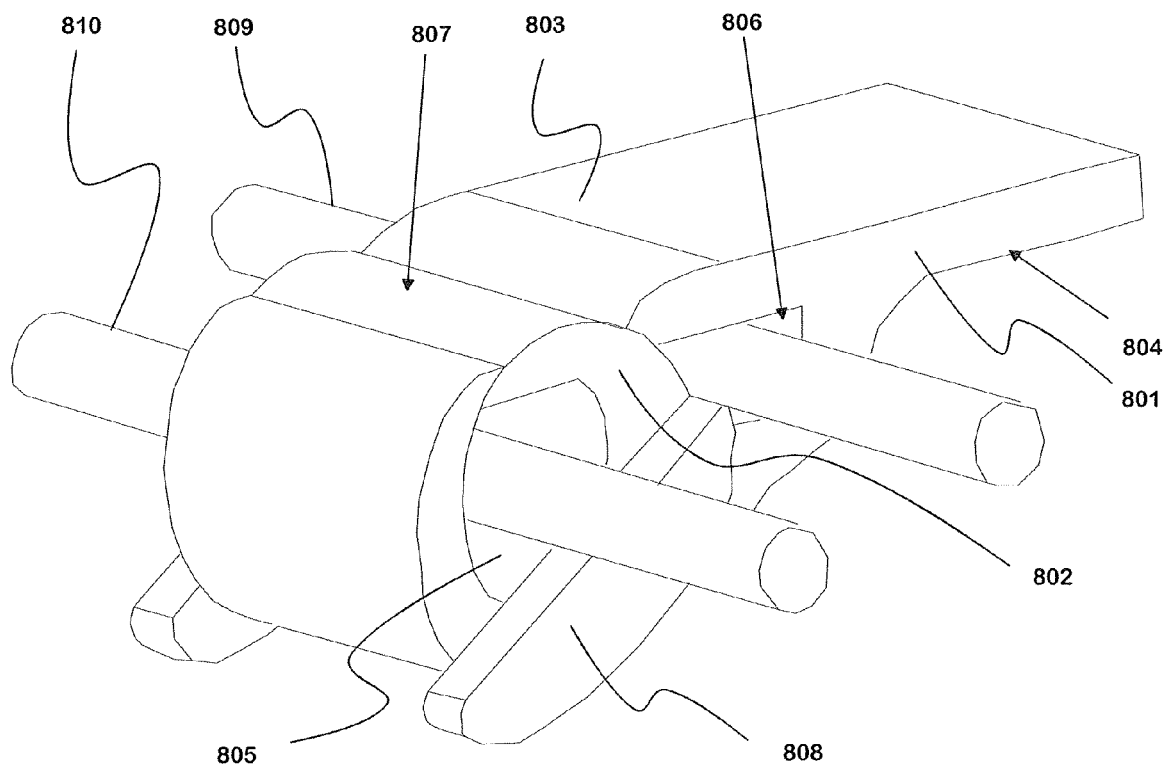
FIG. 8 presents as an example an orthodontic bracket according to the invention, to which bracket two archwires have been attached.

In FIG. 8 is an example of an orthodontic bracket according to the invention in locking position, to which two archwires has been attached. The orthodontic bracket has a body portion 801, a locking portion 802, a surface 803 facing away from the tooth, a surface 804 against the tooth, setting slot 805 and an archwire slot 806. There is an opening 807 on the surface facing away from the tooth. There is a lever system 808 in the locking portion. Two archwires have been attached to the orthodontic bracket: a first archwire 809 and a second archwire 810. The archwire is advantageously metal and it can have a circular or angular cross section. In some stages of the orthodontic process the archwire can have the same shape as the archwire slot. In that case the archwire sits tightly in the archwire slot. The first archwire is in the archwire slot and the second archwire is in the setting slot. The orthodontic bracket is in locking position, whereupon the archwire slot, setting slot and the opening on the surface facing away from the tooth are closed. Then the locking portion keeps the first and the second archwire in place. The archwires are generally under strain and they focus force on the orthodontic bracket and the tooth, onto which the orthodontic bracket is attached. The amount and direction of the force can be controlled with the properties of the archwire, such as rigidity, size and material and with orientations and positions of the archwire slot or setting slot in the orthodontic bracket. In addition to the archwire or archwires or instead of the them tighteners, that are usually made from some elastic material, can be used. The tightener is attached between two orthodontic brackets. With them traction is caused between the orthodontic brackets. The tighteners are usually loops or the like. The tightener can be attached to the archwire slot or the setting slot. Advantageously it can be attached even if there is an archwire in the slot. In some embodiments a groove can be made to the outer surface of the orthodontic bracket in which the part of the tightener loop running on the outer surface of the orthodontic bracket can be placed.

Figure 9A:
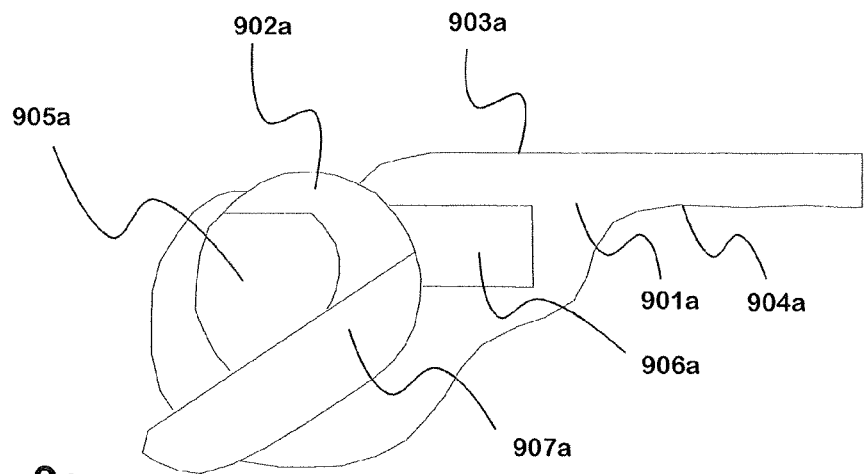
FIGS. 9a, 9b and 9c present examples of different positions of an archwire slot of an orthodontic bracket according to the invention.
Figure 9B:
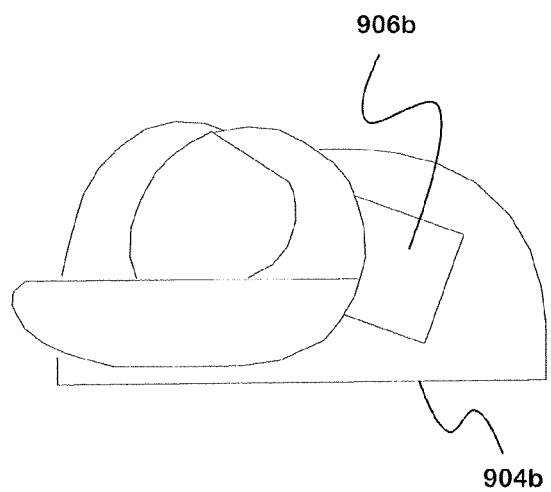
Figure 9C:
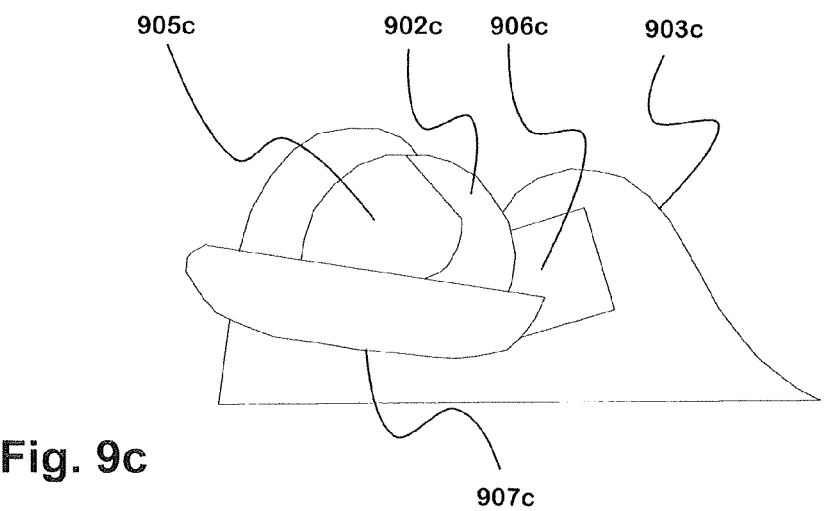

In FIGS. 9a, 9b and 9c there are three examples of placement of the archwire slot of the orthodontic bracket according to the invention in different types of orthodontic brackets. The orthodontic brackets of the examples have a body portion 901, a locking portion 902, a surface 903 facing away from the tooth, a surface 904 against the tooth, setting slot 905 and an archwire slot 906 and a lever system 907 for rotating the locking portion. In the cases according to the examples the archwire slots are perpendicular. The orthodontic brackets are in locking position.

In FIG. 9a there is an example of an orthodontic bracket which is meant for the rear surface of the incisor. The surface 904a against the tooth is formed according to the profile of the tooth. The side walls of the archwire slot 906a are substantially parallel to the surface 903a facing away from the tooth on top of the archwire slot. The archwire can be oriented in other ways, such as for example so that its walls are oblique in relation to the surfaces of the orthodontic bracket. Advantageously the orthodontic bracket is placed on the surface of the tooth so that that end of the orthodontic bracket in which the locking portion is, is placed towards the gingiva. The thicker end of the orthodontic bracket is then closer to the gingiva. Then the orthodontic bracket interfere the tongue as little as possible and the locking portion is better protected.

In FIG. 9b there is an example of an orthodontic bracket which is meant for the front surface of the tooth. The surface 904b against the tooth is now nearly straight. The archwire 906b is tilted towards the surface 904b against the tooth. The angle of the archwire slot in relation to the surface against the tooth depends on what position the root of the tooth is wanted to settle in relation to the trans-verse direction of the archwire.

In FIG. 9c there is an example of an orthodontic bracket which is meant for the side areas of the lingual surface of a tooth. In this case the archwire slot 906c is tilted towards the surface 903c facing away from the tooth. Then a benefit can be that the lever system 907c extends over the locking portion 902c also to the opposite side of the setting slot 905c. Then when the locking portion is rotated further the lever system can be adapted to hold even a smaller archwire tighter in place in the archwire slot when the lever system comes into contact with the archwire.

Figure 10:
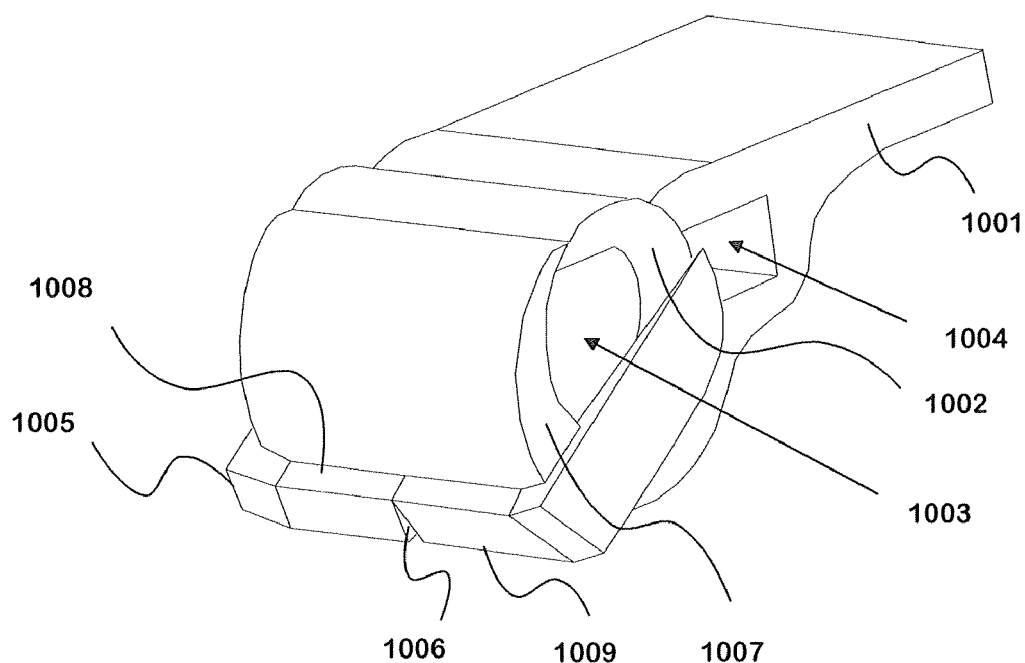
FIG. 10 presents an example of a locking arrangement of a locking portion of an orthodontic bracket according to the invention.

In FIG. 10 there is an example of the locking arrangement of the orthodontic bracket's locking portion according to the invention. In the orthodontic bracket according to the example there is a body portion 1001, a locking portion 1002, a setting portion 1003 and an archwire slot 1004. The locking portion is in the locking portion slot situated in the body portion. The locking portion has substantially the same width as the locking portion slot. There is a locking mechanism 1005 in the locking portion, which can be used as a lever arrangement for rotating the locking portion. The locking mechanism is an elongated, substantially plate-like structure. This is also attached to the locking portion on its both sides so that by rotating it also the locking portion rotates. The surface of the locking mechanism on the side of the orthodontic bracket is substantially on the same level as the body portion's sides and the surface. The locking mechanism goes round from one side of the locking portion over the outer surface of the body portion to the other side of the locking portion. In the part of the locking mechanism extending over the outer surface of the body portion there is a first side 1008 and a second side 1009 that are substantially parallel with the longitudinal axis of the locking portion slot. When the orthodontic bracket is in transfer position, the locking mechanism extends over the body portion near the opening on the surface facing away from the tooth. When the orthodontic bracket is in standby position, the locking mechanism is rotated so that its portion going round the body portion is further from the opening on the surface facing away from the tooth than in transfer position. In both positions the first side is closer to the edge of the opening than the second side. In locking position the portion of the locking mechanism going around the outer surface of the body portion is near the surface of the tooth when the orthodontic bracket is in place on the surface of the tooth.

On both side walls of the end on the side of the locking portion of the body portion 1001 there is a wedge-shaped protrusion 1007, on the lower end, or in other words at the ends closest to the surface of the tooth, of which there is a drop towards the side edge of the body portion The protrusions are placed so that the locking mechanism passes them when it is moved to the locking position. The portion of the locking mechanism 1005 going round the outer surface of the body portion 1001 is divided in half with a gap 1006. This is located substantially in the middle of the locking mechanism. When the locking mechanism is moved from the standby position towards the locking position, the parts on the sides of its body portion slide on top of the protrusions and they are lifted off the surface of the body portion. Then the gap in the locking mechanism widens and the parts touching each other detach from one another. When the first side of the locking mechanism has passed the protrusion it returns back in contact with the surface of the body portion and the gap returns to the state in which it was before the locking mechanism started to go over the protrusion. Because the side on the side of the tooth is steep, the locking mechanism does not return easily over the protrusion towards the top of the orthodontic bracket or in other words towards the surface facing away from the tooth. Advantageously the protrusion is situated so that the locking mechanism is in locking position after it has crossed the protrusion. The locking mechanism can be released from the locking position by focusing force on the gap for example with some means with which it can be widened. The direction can be for example upwards from the surface of the orthodontic bracket below the locking mechanism. Then the parts of the locking mechanism against the sides of the body portion rise off the surface of the body portion and the locking mechanism can be moved over the steep side of the protrusion and the locking portion is released. After this the locking mechanism can be moved for example into standby position or transfer position.

Figure 11:
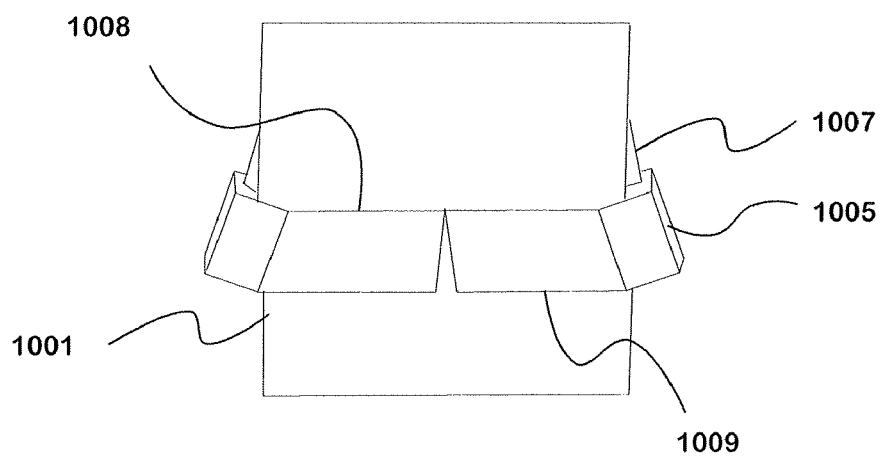
FIG. 11 presents the orthodontic bracket presented in FIG. 10 seen from the gingival end

In FIG. 11 there is depicted the orthodontic bracket of FIG. 10 seen from the end on the side of the locking portion slot. The locking mechanism 1005 is in locking position or in other words its part going round the body portion 1001 is on the side of the tooth of the protrusions 1007 so that the first side 1008 of the locking mechanism is against the steep side of the protrusion. It is possible to place more protrusions so that they stop the locking mechanism in locking position from moving further towards the surface of the tooth. When the locking mechanism is moved towards the tooth, these additional protrusions get in contact with the second side 1009 of the locking mechanism and stop the locking mechanism.

Also other solutions can be used to lock and move the locking portion of the orthodontic bracket. For example on the side walls at the end of the body portion 1001 on the side of the locking portion slot grooves can be made instead of protrusions, in which grooves the locking mechanism 1005 sets. The locking mechanism is then released the same way as with the protrusions. The locking portion can be arranged to be locked also in other positions than the locking position. Then in the body portion protrusions or grooves are made in such places that as the locking mechanism stops at them the locking portion is in desired position.

Figure 12:
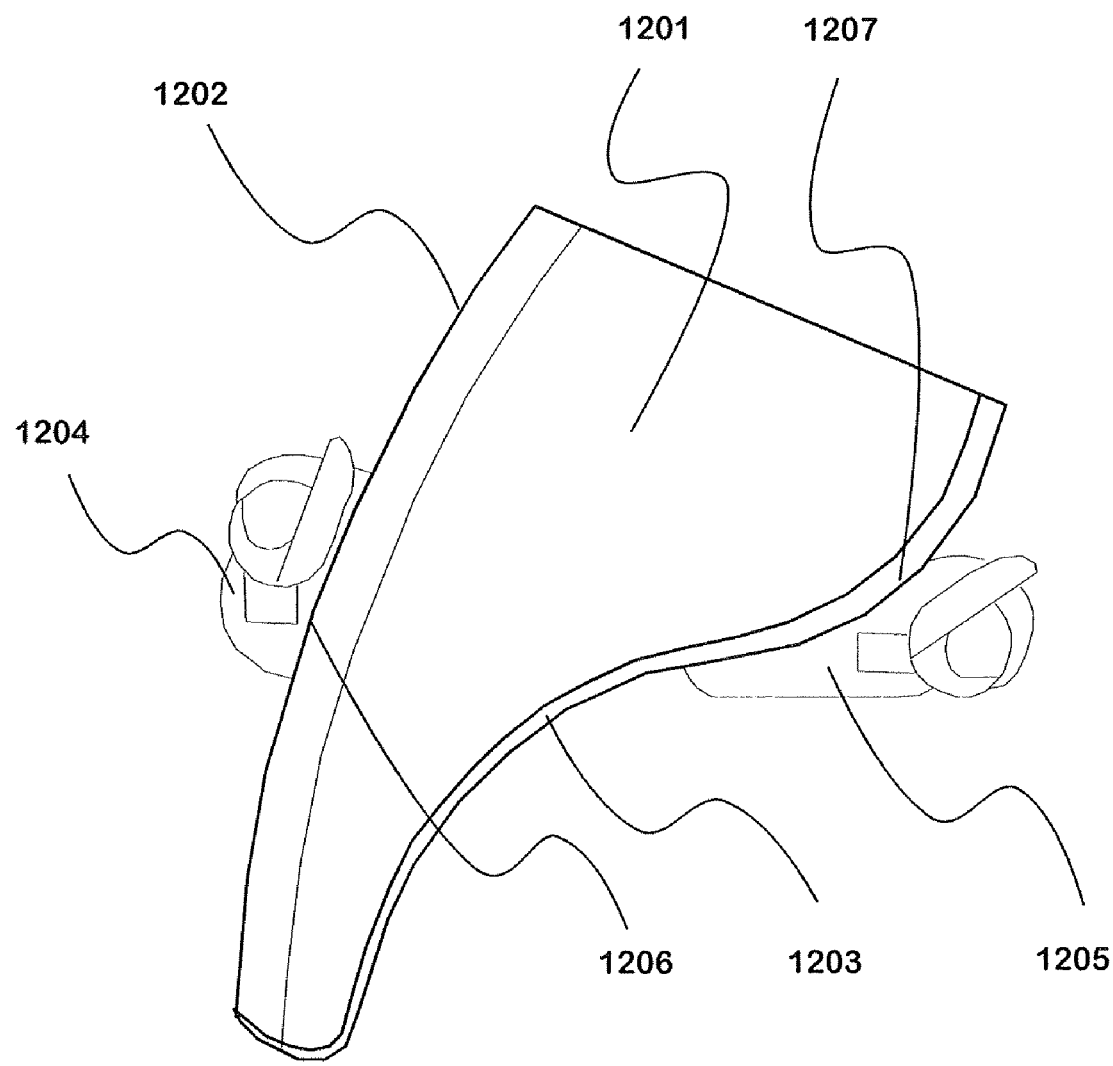
FIG. 12 presents an example of orthodontic brackets according to the invention attached to the different surfaces of the tooth.

In FIG. 12 there is an example of the placement of the orthodontic bracket according to the invention on the surface of a tooth. In the figure there is a tooth 1201, which has a front surface 1202, which is towards the labia and a rear surface 1203, which is towards the pharynx. On the front surface of the tooth has been placed a first orthodontic bracket 1204 and on the rear surface of the tooth a second orthodontic bracket 1205. FIG. 12 is an example of placement of the orthodontic brackets and only very rarely they exist at the same time on both sides of the teeth. Advantageously the orthodontic bracket is placed on the surface of the tooth so that that end of the orthodontic bracket in which the locking portion is, is placed towards the gingiva. The thicker end of the orthodontic bracket is then closer to the gingiva. Then the orthodontic bracket interferes the tongue or the cheeks as little as possible and the locking arrangement of the locking portion is better protected. Since the surface of the tooth is formed differently on different sides—on the front side the tooth is even and on the rear side curved—the surfaces of the orthodontic brackets against the tooth are different on different sides of the teeth. The surface 1206 against the tooth of the first orthodontic bracket is substantially even and the surface 1207 against the tooth of the second orthodontic bracket is at least partially curved.

Figure 13:
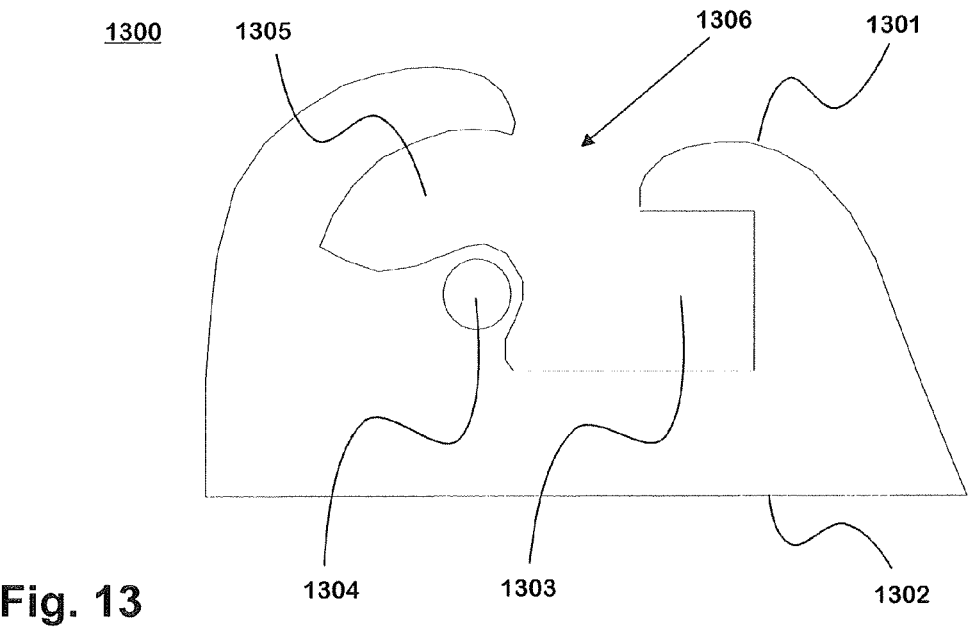
FIG. 13 presents an example of a body portion of an orthodontic bracket according to the invention seen from the side.

FIG. 13 presents an example of the body portion of the orthodontic bracket according to the invention seen from the side. The body portion 1300 has a surface 1301 facing away from the tooth and a surface 1302 against the tooth. In the body portion there is the locking portion slot 1305, which in this case penetrates the whole body portion. There is a archwire slot 1303 in the wall of the locking portion slot. Locking portion slot opens to the surface away from the tooth forming an opening 1306. In the body portion there is an axle hole 1304 of the locking portion. The hole penetrates in this case the whole of the body portion. The hole is substantially parallel to the locking portion slot.

Figure 14:
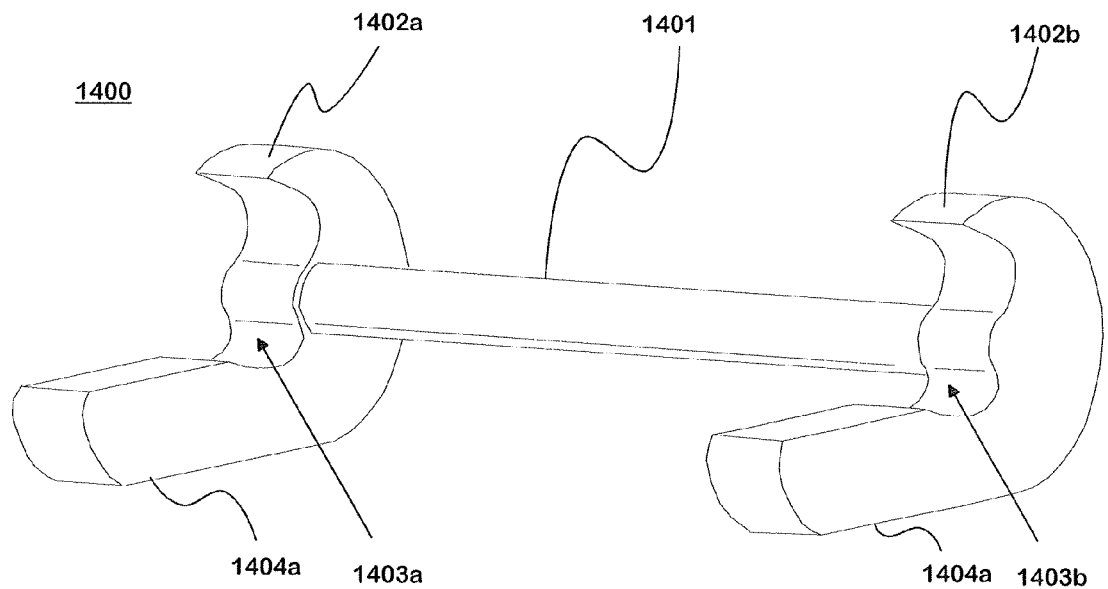
FIG. 14 presents an example of a locking portion of an orthodontic bracket according to the invention.

In FIG. 14 there is an example of the orthodontic bracket's locking portion according to the invention. In the locking portion 1400 there is an locking portion axle 1401 and a first end portion 1402a and a second end portion 1402b. In the first end portion there is a first setting slot 1403a and a first lever system 1404a. In the second end portion there is a second setting slot 1403a and a second lever system 1404b. The end portions are substantially laminar structures that have been attached to the locking portion axle. The attachments to the axle may have been made fixed or so that the end portions can be moved to different position in relation to each other. In the case of the figure the end portions are in the same position. The setting slots run through the end portions.

Figure 15:
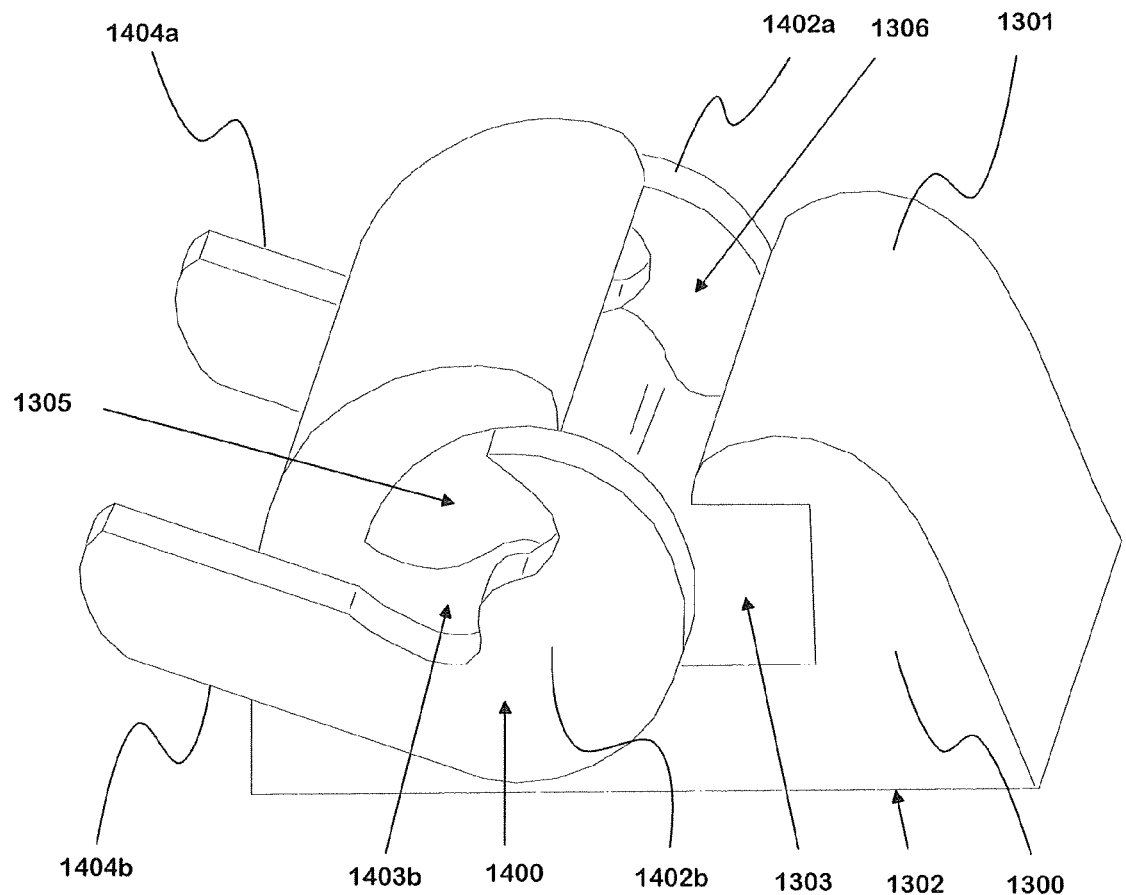
FIG. 15 presents an example of an orthodontic bracket according to the invention, in which there are the body portion and the locking portion according to the FIGS. 13 and 14.

FIG. 15 there is an example of an orthodontic bracket according to the invention, in which there are the body portion and the locking portion according to the FIGS. 13 and 14. In the orthodontic bracket there is a body portion 1300 and locking portion 1400. The orthodontic bracket has a surface 1301 facing away from the tooth and a surface 1302 against the tooth. In the body portion there is a locking portion slot 1305. Locking portion slot opens to the surface away from the tooth so that an opening 1306 is formed. There is a archwire slot 1303 in the wall of the locking portion slot. In the body portion there is a hole for the locking portion axle. The locking portions is attached to the body portion so that the locking portion axle is in said hole. The attachment has been made so that the locking portion can be moved around its axis.

In the locking portion 1400 there is a first end portion 1402a and a second end portion 1402b. The end portions have been attached to the locking portion axle. The end portions are against the sides of the body portion 1300. In this case there are no moving parts in the locking portion slot. The first and second end portion can be attached to the locking portion axle either fixed or movably or so that the one end portion is attached movably and the other fixed. If the attachment is fixed, the end portions move as the lever systems 1404a or 1404b are moved. When the attachment is movable, the end portions can be placed in different positions with the lever systems. This can be beneficial for example in the following case. When the locking portion is in standby position the first setting slot 1403a and the second setting slot 1403b are towards the extension determined by the opening 1306 on the surface facing away from the tooth. The archwire is placed through the opening to the setting slots. The locking portion is turned to the transfer position, whereupon the setting slots are oriented towards the extension determined by the archwire slot. Then the archwire can be transferred from the setting slots to the archwire slot. Moving to the locking position can be made in two phases. The archwire is moved to the archwire slot from near the first setting slot. After this the first end portion is moved to the locking position while the second end portion is still in transfer position. Then the first end portion keeps the archwire in place in the archwire slot. The archwire is moved to the archwire slot from another setting slot and after this the second end portion is moved to locking position. Placing the additional tighteners is made by moving the locking portion from both of its ends to standby position and after the tighteners have been placed by moving the locking portion into locking position.

Figure 16:
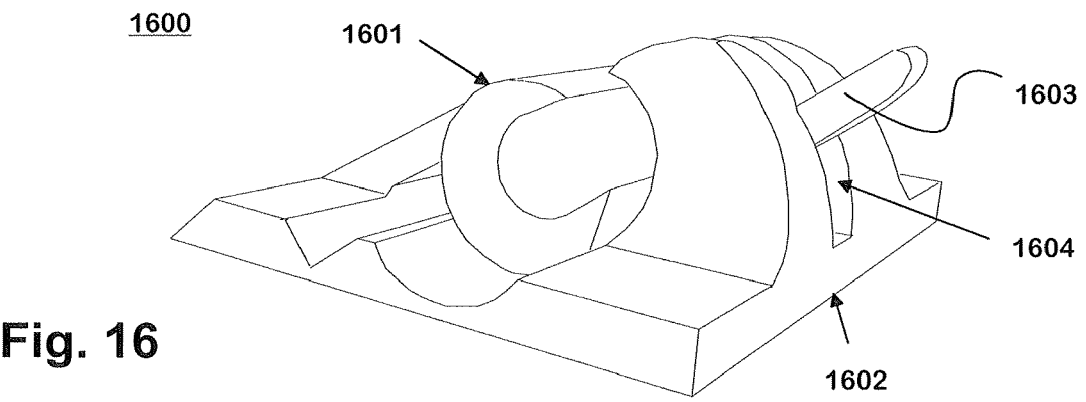
FIG. 16 presents an example of an orthodontic bracket according to the invention.

FIG. 16 there is an example of an orthodontic bracket 1600 according to the invention, in which there are a body portion 1602 and a locking portion 1601. In the locking portion there is a lever system 1603. In the body portion there is a lever system slot 1604, into which the lever system is arranged to set when the locking portion is rotated to locking position. The lever system slot is in this example substantially in the middle of the body portion and transversely in relation to the locking portion slot.

Figure 17:
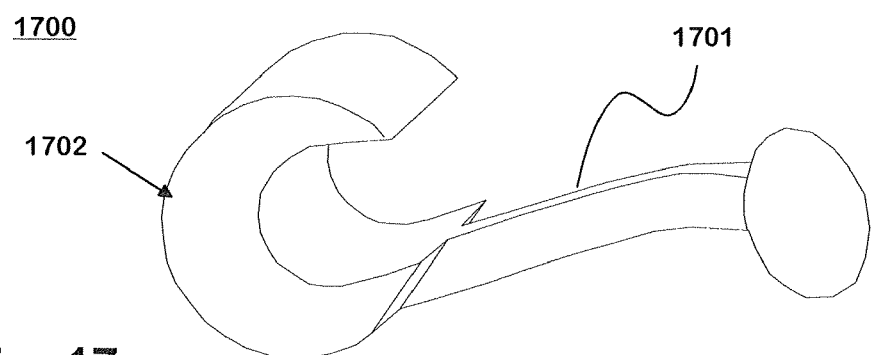
FIG. 17 presents an example of a locking portion of an orthodontic bracket according to the invention.
Figure 18:
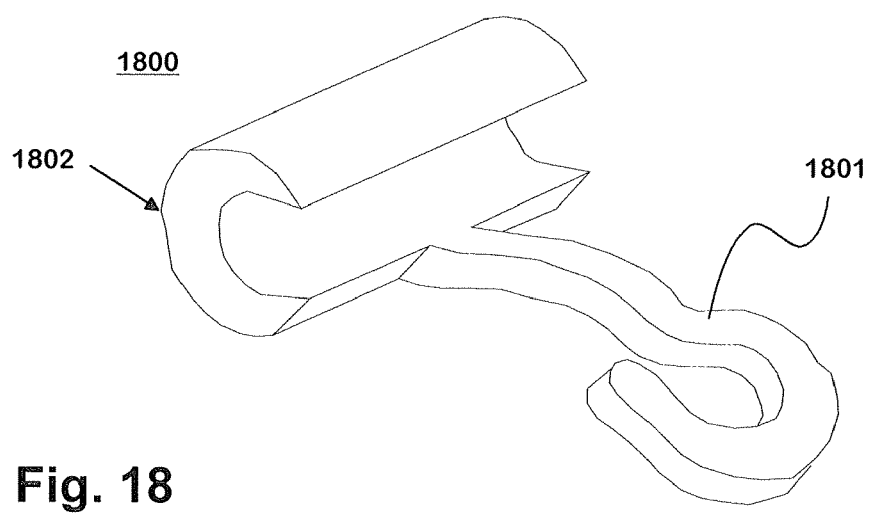
FIG. 18 presents an example of a locking portion of an orthodontic bracket according to the invention.
Figure 19:
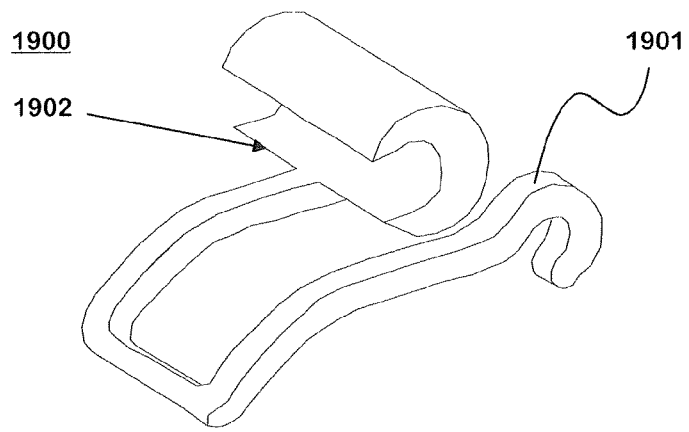
FIG. 19 presents an example of a locking portion of an orthodontic bracket according to the invention.

In FIG. 17 there is an example of a locking portion 1700 of an orthodontic bracket according to the invention, in which there is a lever arrangement 1701. In the end of the lever arrangement there is a knob-like portion both for making moving it easier and for facilitating the attachment of a tightener to the lever arrangement. In FIG. 18 there is an example of a locking portion 1800 of an orthodontic bracket according to the invention, in which there is a lever arrangement 1801. At the end of the lever arrangement there is a hook-like structure to which a tightener can be attached. The opening direction of the hook-like structure can vary according to which way the tightener is meant to be placed. In FIG. 19 there is an example of a locking portion 1900 of an orthodontic bracket according to the invention, in which there is a lever arrangement 1901. The lever arrangement is formed so that the lever arrangement itself can act as a tightener focusing force to the orthodontic bracket. There is a hook at the end of the lever arrangement to which tighteners can be attached.

Figure 20:
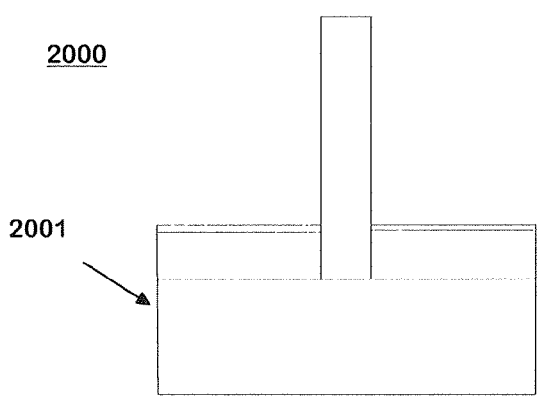
FIG. 20 presents an example of a locking portion of an orthodontic bracket according to the invention.
Figure 21:
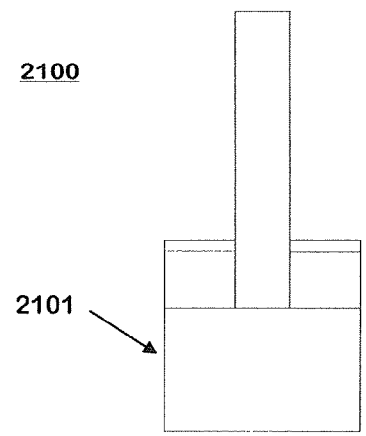
FIG. 21 presents an example of a locking portion of an orthodontic bracket according to the invention.
Figure 22:
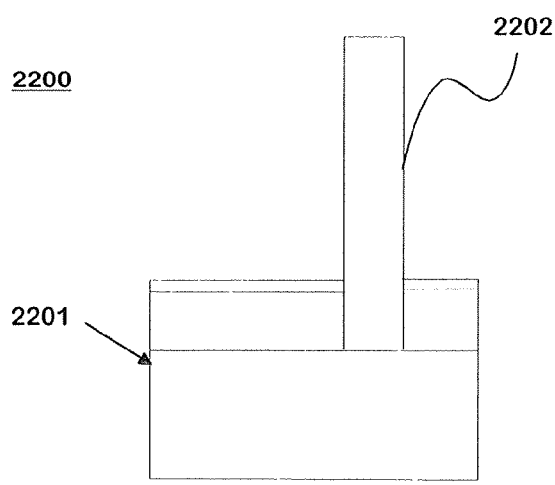
FIG. 22 presents an example of a locking portion of an orthodontic bracket according to the invention.
Figure 23:
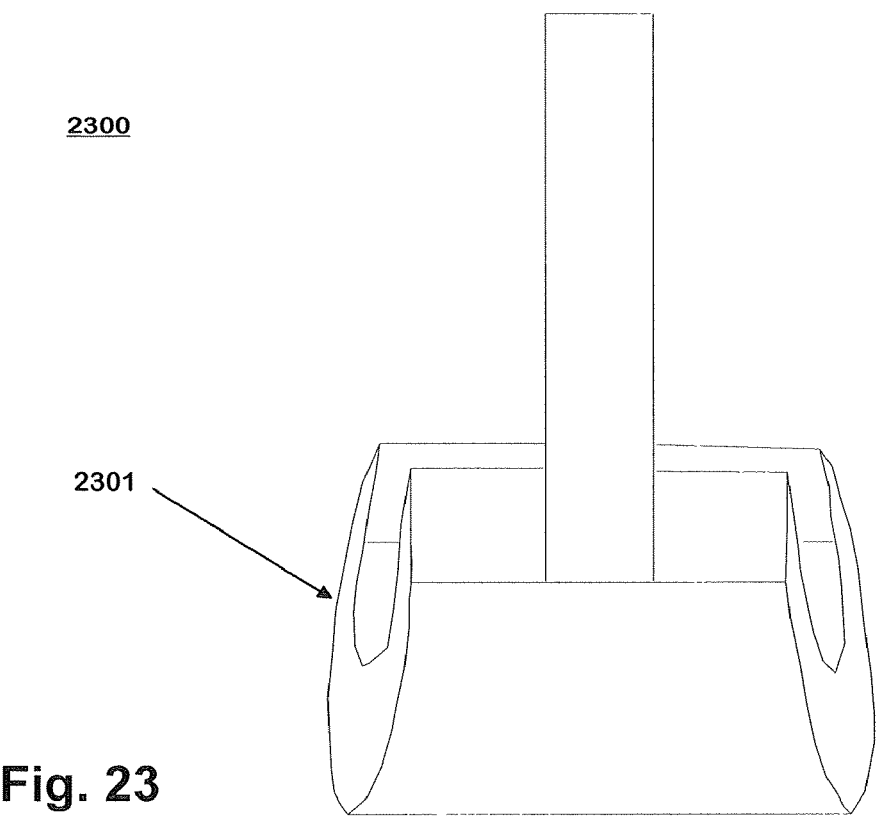
FIG. 23 presents an example of a locking portion of an orthodontic bracket according to the invention and, FIG. 24 presents an example of a locking portion of an orthodontic bracket according to the invention.
Figure 24:
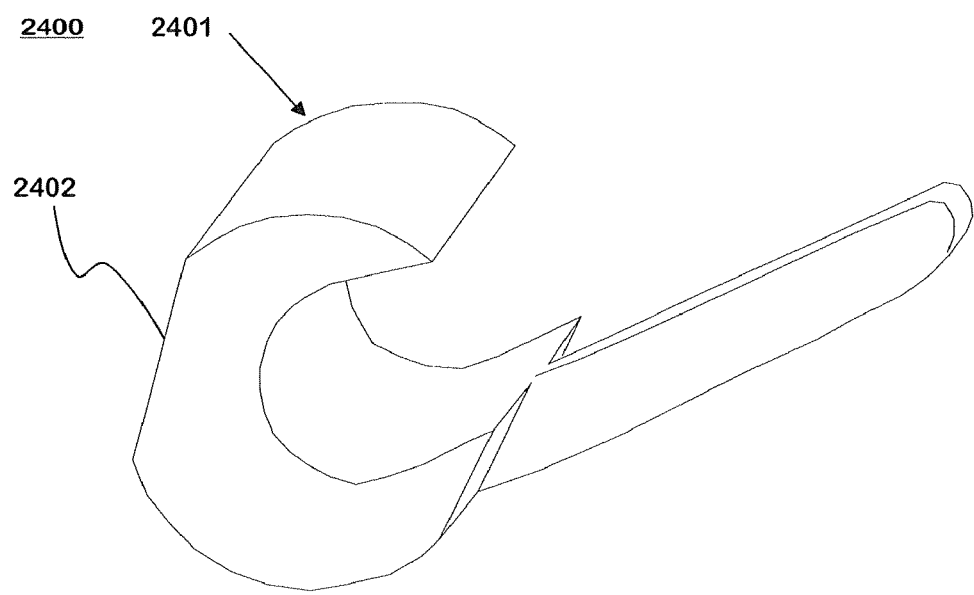

In FIGS. 20-24 there are examples of a forming at the locking portion slot of the locking portion and how it is used to focus force of the archwire to the orthodontic bracket in different ways. In FIG. 20 there is an example of a locking portion 2000 of an orthodontic bracket according to the invention, in which there is a portion 2001 in the locking portion slot. In this example the portion in the locking portion slot is substantially wide, whereupon it focuses the force of the archwire to the orthodontic bracket along a long distance. In FIG. 21 there is an example of a locking portion 2100 of an orthodontic bracket according to the invention, in which there is a portion 2101 in the locking portion slot. In this the portion in the locking portion slot is substantially narrow, whereupon the locking portion focuses the force of the archwire to the orthodontic bracket along a shorter distance. In FIG. 22 there is an example of a locking portion 2200 of an orthodontic bracket according to the invention, in which there is a portion 2201 in the locking portion slot, which portion is asymmetrical in relation to the placement of the lever arrangement 2202. Then the portion in the locking portion slot is divided into a wider and a narrower portion. The wider side of the portion in the locking portion slot has greater force than the narrower side. In FIG. 23 there is an example of a locking portion 2300 of an orthodontic bracket according to the invention, in which there is a portion 2301 in the locking portion slot. The portion in the locking portion slot is formed so that in locking position its portion on the side of the archwire is wider than the portion on the side of the free surface. In FIG. 24 there is an example of a locking portion 2400 of an orthodontic bracket according to the invention, in which there is a portion 2401 in the locking portion slot. In the portion in the locking portion slot there is an even side 2402. When the locking portion is in locking position a space is formed between this even side and the wall of the locking portion slot that can be used for example to lock a tightener. If the even side is aligned with the archwire slot, it can be used to regulate how deep into the archwire slot the archwire sets and what kind of force it focuses to the orthodontic bracket.

In the foregoing some advantageous embodiments of the invention are described. The invention is not limited to the solutions just described, but the inventive idea can be applied in numerous ways within the limits set by the Claims.

The invention claimed is:

1. Orthodontic bracket comprising:
    a body portion in which there is an archwire slot for archwire;
    a rotatable locking portion;
    surface of the body portion to be positioned against the tooth; and
    surface of the body portion for facing away from the tooth,
    wherein in the body portion there is
        a locking portion slot, which is substantially parallel with the archwire slot and open to the surface of the orthodontic bracket facing away from the tooth, whereupon it forms an opening on said surface and
        said archwire slot is in a wall of the locking portion slot so that an opening of said archwire slot is in the locking portion slot, and
    in the locking portion there is
        at least one setting slot, which slot is arranged when rotating the locking portion to align at least towards the archwire slot or the extension defined by it or towards the opening on the surface facing away from the tooth or the extension defined by it.

2. Orthodontic bracket according to claim 1, wherein the locking portion is attached to the body portion so that the rotational axis of the locking portion is oriented so that the locking portion can be rotated when the archwire is in the setting slot.

3. Orthodontic bracket according to claim 1, wherein the locking portion slot is substantially parallel with the archwire slot.

4. Orthodontic bracket according to claim 1, wherein the locking portion slot is arranged to penetrate the body portion at least partially.

5. Orthodontic bracket according to claim 1, wherein the archwire slot is arranged to function as a tube protecting the end of the archwire.

6. Orthodontic bracket according to claim 1, wherein in the locking portion there is a lever arrangement for rotating the locking portion.

7. Orthodontic bracket according to claim 1, wherein to the locking portion a means can be attached for rotating the locking portion.

8. Orthodontic bracket according to claim 1, wherein in the surface of the body portion there are recesses for improving the attachment of the orthodontic bracket to the tooth.

9. Orthodontic bracket according to claim 8, wherein on the sides of the body portion there are recesses for improving the attachment of the orthodontic bracket to the tooth.

10. Orthodontic bracket according to claim 1, wherein the setting slot is such that one or several tighteners or archwires or one or several of both can be fitted in said setting slot.

11. Orthodontic bracket according to claim 1, wherein there is a locking mechanism in the orthodontic bracket, with which the locking portion can be locked at least to such a position that the locking portion closes at least partially the archwire slot.

12. Orthodontic bracket according to claim 11, wherein the locking mechanism is implemented with the body portion and the locking portion.

13. Orthodontic bracket according to claim 1, wherein said orthodontic bracket can be attached both to the front surfaces and rear surfaces of the tooth.

14. Arrangement for correcting irregularities of the teeth, comprising:
orthodontic brackets to be attached to the teeth, comprising:
a body portion in which there is an archwire slot for archwire;
a rotatable locking portion;
a surface of the body portion to be positioned against the tooth; and
a surface of the body portion for facing away from the tooth and
an archwire to focus force to the orthodontic brackets,
wherein in the body portion of the orthodontic brackets there is
a locking portion slot, which is substantially parallel with the archwire slot and is arranged to form an opening on the surface of the orthodontic bracket facing away from the tooth, and
said archwire slot is in a wall of the locking portion slot so that an opening of said archwire slot is in the locking portion slot, and
in the locking portion there is
at least one setting slot,
and the locking portion is arranged to be rotatable into at least two of the following positions:
standby position, in which the setting slot is towards the opening on the surface facing away from the tooth or towards the extension determined by it,
transfer position, in which the setting slot is towards the archwire slot or towards the extension determined by it, or
locking position, in which the locking portion closes the archwire slot at least partially.

15. Arrangement according to claim 14, wherein the locking portion is attached to the body portion so that the rotational axis of the locking portion is oriented so that the locking portion can be rotated when the archwire is in the setting slot.

16. Arrangement according to claim 14, wherein the orthodontic bracket is arranged so that the unattached archwire can be placed to the setting slot of the locking portion when the locking portion is in standby position, and the archwire can be placed in the archwire slot when the locking portion is in transfer position, and that in locking position the locking portion is arranged to keep the archwire in place in the archwire slot.

17. Arrangement according to claim 14, wherein in standby position the locking portion is arranged to close the archwire slot at least partially.

18. Arrangement according to claim 14, wherein the orthodontic bracket is arranged so that in the standby position of the locking portion one or several tighteners or another archwire or one or several of both can be placed into the setting slot of the locking portion.

19. Arrangement according to claim 14, wherein the orthodontic bracket is arranged so that the locking portion can be rotated from standby position to locking position without it being in the transfer position there in between.

20. Arrangement according to claim 14, wherein the archwire set in place is arranged to focus force to the orthodontic brackets.

21. Arrangement according to claim 14, wherein the size and shape of the orthodontic brackets can be adapted for each tooth.

22. Arrangement according to claim 14, wherein the archwire slot can be placed in the body portion in different orientations for each orthodontic bracket to focus different kind of forces to the tooth.

23. Arrangement according to claim 14, wherein said arrangement can be placed on the front surfaces or the rear surfaces of the teeth.

* * * * *